United States Patent
Dunlop et al.

(10) Patent No.: US 8,714,004 B2
(45) Date of Patent: May 6, 2014

(54) MEASURING GAS CONTENT OF UNCONVENTIONAL RESERVOIR ROCKS

(75) Inventors: Erik Christopher Dunlop, Adelaide (AU); Peter John Archer, Adelaide (AU); Mika Olavi Porter, Osborne Park (AU)

(73) Assignee: Santos Ltd. (AU)

( * ) Notice: Subject to any disclaimer, the term of this patent is extended or adjusted under 35 U.S.C. 154(b) by 0 days.

(21) Appl. No.: 13/522,201

(22) PCT Filed: Jan. 13, 2011

(86) PCT No.: PCT/AU2011/000032
§ 371 (c)(1),
(2), (4) Date: Mar. 6, 2013

(87) PCT Pub. No.: WO2011/085444
PCT Pub. Date: Jul. 21, 2011

(65) Prior Publication Data
US 2013/0152665 A1    Jun. 20, 2013

(30) Foreign Application Priority Data
Jan. 13, 2010   (AU) ................................ 2010900120

(51) Int. Cl.
E21B 49/08   (2006.01)
E21B 47/00   (2012.01)
G01N 33/24   (2006.01)

(52) U.S. Cl.
USPC ........................... 73/152.23; 175/50; 73/19.09

(58) Field of Classification Search
USPC ............ 96/155; 175/5, 50, 58, 59; 73/152.08, 73/152.09, 152.18, 152.19, 152.43, 152.46
See application file for complete search history.

(56) References Cited

U.S. PATENT DOCUMENTS 3,898,061 A  *  8/1975  Brunato .......................... 96/196
4,381,191 A  *  4/1983  Brand et al. .................... 96/198
(Continued)

FOREIGN PATENT DOCUMENTS

WO    WO 2010111726    10/2010

OTHER PUBLICATIONS

Katja U. Heeschen, Hans Jürgen Hohnberg, Matthias Haeckel, Friedrich Abegg, Manuela Drews, Gerhard Bohrmann, "In situ hydrocarbon concentrations from pressurized cores in surface sediments, Northern Gulf of Mexico," Marine Chemistry, vol. 107, Issue 4, Dec. 20, 2007, pp. 498-515.*

*Primary Examiner* — Lisa Caputo
*Assistant Examiner* — Punam Roy
(74) *Attorney, Agent, or Firm* — The Farrell Law Firm, P.C.

(57) ABSTRACT

A method of measuring the in-situ Total Gas content of an unconventional reservoir rock, the method including: drilling a borehole through a measurement interval in the reservoir to generate an annular volume of drilling mud that includes cuttings and gas, the annular volume having a leading edge and a trailing edge; diverting the leading edge of the annular volume such that all of the annular volume is captured in a degassing storage system without being exposed to atmosphere; discontinuing the diversion of the annular volume when the trailing edge of the annular volume has been captured in the degassing storage system; measuring the gas volume in the degassing storage system to determine the amount of gas per annular volume; and calculating the in-situ Total Gas content of the reservoir with reference to the amount of gas and cuttings per annular volume.

25 Claims, 2 Drawing Sheets

(56) References Cited

U.S. PATENT DOCUMENTS

| | | | |
|---|---|---|---|
| 4,666,471 A | 5/1987 | Cates | |
| 5,785,131 A | 7/1998 | Gray | |
| 5,928,519 A | 7/1999 | Homan | |
| 6,276,455 B1 * | 8/2001 | Gonzalez | 166/357 |
| 6,389,878 B1 * | 5/2002 | Zamfes | 73/19.09 |
| 7,465,426 B2 * | 12/2008 | Kerherve et al. | 422/68.1 |
| 7,748,266 B2 * | 7/2010 | Evrard et al. | 73/152.23 |
| 2004/0031622 A1 * | 2/2004 | Butler et al. | 175/5 |
| 2008/0115971 A1 * | 5/2008 | Kelleher et al. | 175/5 |
| 2009/0199618 A1 * | 8/2009 | Evrard | 73/19.09 |
| 2009/0288880 A1 * | 11/2009 | Wojcik et al. | 175/50 |
| 2011/0308391 A1 * | 12/2011 | DeGreeve et al. | 95/260 |
| 2012/0217065 A1 * | 8/2012 | Gray | 175/50 |
| 2013/0311096 A1 * | 11/2013 | Greer et al. | 702/9 |

* cited by examiner

MEASURING GAS CONTENT OF UNCONVENTIONAL RESERVOIR ROCKS

PRIORITY

This application is a National Phase Entry of PCT International Application No. PCT/AU2011/000032, which was filed on Jan. 13, 2011, and claims priority to Australian Patent Application No. 2010900120, which was filed on Jan. 13, 2010, the content of each of which is incorporated herein by reference.

FIELD OF THE INVENTION

The present invention relates generally to the measurement of the Total Gas content of unconventional reservoir rocks, such as the unconventional gas reservoirs which may occur in sedimentary, igneous or metamorphic rock.

More particularly, the present invention relates to a method and apparatus for the measurement of the in-situ Total Gas content of an unconventional gas reservoir, being a gas reservoir such as a tight sandstone gas reservoir, a shale gas reservoir, a coal seam gas reservoir, a hydrate gas reservoir, or the like. While the following description relates primarily to this particular application, it will be appreciated that the present invention is not to be so limited and may for instance be applicable to the measurement of the Total Gas content in an unconventional oil reservoir.

BACKGROUND OF THE INVENTION

Declining production from conventional hydrocarbon reservoirs, coupled with increasing demand for energy worldwide, has resulted in a major shift towards the commercialisation of unconventional hydrocarbon resources (those that require greater than industry-standard levels of technology or investment). This paradigm shift has been facilitated by a combination of higher gas prices and key technological breakthroughs over the last 20 years or so. Unconventional gas is at the forefront relative to unconventional oil due to its geographical abundance and the fact that its use as a fuel is more environmentally friendly than the combustion of oil or coal. Indeed, gas is often thought of as being a "transition fuel" in advance of cleaner, renewable alternatives.

Conventional hydrocarbon reservoirs are those that can be produced at economic flow rates and that will produce economic volumes of hydrocarbons without the assistance of large stimulation treatments or special recovery processes. These are high to medium permeability reservoirs in which a vertical well can be drilled by a conventional drilling rig, a pay interval perforated and the well produced at commercial flow rates, recovering economic volumes of hydrocarbons with minimal assistance. An unconventional hydrocarbon reservoir is one that cannot be produced at economic flow rates or that does not produce economic volumes of hydrocarbons without the assistance of massive stimulation treatments or special recovery processes and technologies, such as steam injection. Typical unconventional reservoirs are tight sandstone gas, shale gas, coal seam gas, hydrate gas and heavy oil.

Conventional drilling rigs that are used to create the borehole generally include a drilling mud circulation system, where a suitable drilling fluid (generally referred to as "drilling mud") is circulated under high pressure down through a hollow drill string (a jointed metal pipe), to a point at or near the advancing face of the borehole, and then back up to surface via the annular space (often simply referred to as "the annulus") formed between the drill pipe and the borehole wall. The drilling mud acts to cool the drill bit and remove the cuttings during drilling, and also acts to suspend the cuttings while drilling is paused. The drilling mud returned to surface in this manner includes the cuttings (which would subsequently be separated so the drilling mud can be re-used), but also any gas that enters the borehole from whatever geological features are passed through (including both known and unknown hydrocarbon reservoirs) during the drilling.

During a normal drilling operation, when the drilling mud reaches surface it passes through a large valve capable of sealing and isolating the borehole to stop formation (i.e. geological) fluids entering the borehole (with potentially hazardous expulsion at surface) when high pressure zones are encountered which exceed the confining hydrostatic pressure of the drilling mud in the borehole. This device is often referred to as a "blowout preventer", or a "BOP". At the top of the blowout preventer, the drilling mud enters a flow diversion device (often referred to as a "bell nipple"). From here, the drilling mud enters a flow line which transports it by gravity to a series of drilling mud storage tanks.

A bell nipple is a section of large diameter pipe, fitted to the top of the blowout preventer and open to atmosphere, to which is attached the flow line via a side outlet. Before reaching the drilling mud storage tanks, the drilling mud is exposed to whatever separation, collection and/or treatment equipment is required, such as screens and sieves to remove the cuttings, filters to remove silt and sand, and purifiers to extract reusable drilling mud that can then be recirculated (as mentioned above) down through the hollow drill string to a point at or near the advancing face of the borehole. Additionally, any gas contained in the drilling mud is allowed to vent to atmosphere via the bell nipple, and at various other locations further downstream, culminating at the drilling mud storage tanks. Drilling mud in this system can be referred to as "recirculated drilling mud".

It will be appreciated that the main function of the blowout preventer is to be able to seal the borehole (or more particularly the annulus) before or after drilling, or when drilling is paused, to prevent liquids and gases from unintentionally escaping. However, during drilling the blowout preventer will remain open to allow the passage therethrough of the drilling mud in order to permit the drilling mud circulation system to operate normally.

There will normally be a zone of interest that is targeted by the drilling, with the aim of directing the drilling such that the borehole passes through that zone of interest.

One of the major challenges in conducting an economic assessment of most unconventional gas play resources is the high uncertainty associated with current techniques for measuring the in-situ Total Gas content of a zone of interest in a targeted geological reservoir. This is particularly the case for deeper reservoirs.

The gas content of unconventional reservoirs is generally regarded as being divided into three components:

Total Gas=Free Gas+Adsorbed Gas+Solution Gas

Free Gas exists in pore space, natural fractures or cleats (in the case of coal); Adsorbed Gas exists in a semi-liquid, monolayered state, bound typically but not exclusively to organic carbon by weak Van der Waals intermolecular forces; and Solution Gas is dissolved in formation water, liquid hydrocarbon, or a combination of both. Solution Gas can be quite significant in some oil reservoirs. With regard to typical unconventional gas play resources, in tight sandstone it is the Free Gas that forms the bulk of the Total Gas content, whereas in shale the Free Gas and Adsorbed Gas components are generally comparable. In contrast, in coal it is the Adsorbed Gas that predominates, although there may be a significant Free Gas contribution.

The techniques most often adopted in order to estimate the in-situ Total Gas content of an unconventional gas reservoir (or one of the above components of Total Gas) are as follows:

1. Mudlogs—this technique provides a qualitative indication of Total Gas, impacted by numerous drilling parameters.
2. Desorption (i.e. degassing) of conventional core or cuttings obtained during a drilling operation—this technique attempts to quantify Total Gas.
3. Porosity/water saturation from conventional core or cuttings obtained during a drilling operation—this technique attempts to quantify the Free Gas in pore spaces.
4. Porosity/water saturation from conventional electric logs—this technique also attempts to quantify the Free Gas in pore spaces.
5. "Unconventional" electric logs—use of these provides an ability to quantify both the Free Gas in pore spaces and the Adsorbed Gas in terms of Total Organic Carbon (TOC), thereby providing a measure of the Total Gas.
6. Adsorption isotherms performed on conventional core or cuttings obtained during a drilling operation—this technique quantifies the Adsorbed Gas.
7. Pressure core techniques—these are generally able to quantify the Total Gas in a reservoir, relying on the trapping of gas in a sealed container at bottom-hole pressures in a well and the subsequent raising of the container (typically at thousands of psi gas pressure) to surface.

Options 1 to 5 above tend to have a high degree of uncertainty for a variety of different reasons. Option 6, although generally accurate, tends to provide only one component of the Total Gas content, which for many types of unconventional gas reservoirs is not particularly useful. Finally, while option 7 is the most accurate for providing an estimation of the Total Gas content of an unconventional gas reservoir, such techniques are currently problematic due to a) availability, b) logistics, c) cost, d) complexity, e) safety and f) mechanical success rate.

Turning to a more specific discussion of the more common types of unconventional gas reservoirs and their normal gas measurement options, for coal seam gas reservoirs Option 2 (relying on the canister desorption of conventional core) has so far been the most widely used approach for measuring Total Gas in these relatively shallow reservoirs (less than approximately 3,000 feet). Unfortunately though, despite efforts to bring the core to surface as quickly as possible, the core retrieval time negatively impacts on the amount of gas captured in the desorption canisters at surface. This typically results in an underestimated in-situ Total Gas content. Indeed, during retrieval, the surrounding drilling mud hydrostatic confining pressure decreases and gas thus escapes from the core.

To compensate, a "Lost Gas" correction must be applied, which is normally done by extrapolating the early-time degassing trend, measured as close as possible to reservoir temperature in desorption canisters at surface, back to "time zero". The latter is defined as the point in time at which the pressure differential across the drilling mud-core interface changes from overbalance to underbalance and gas starts to escape. The deeper the cored zone, the longer the retrieval time, and hence the larger is the proportion and uncertainty of the Lost Gas component. The high uncertainty associated with Lost Gas determination is a major deficiency in this approach.

For shale gas reservoirs, the Total Gas has typically previously been determined by combining options 3, 4 or 5 above with option 6, which has the effect of adding Free Gas and Adsorbed Gas to provide a result for the Total Gas. For these reservoirs, desorption is considered unreliable, again due to the large Lost Gas component associated with retrieving core from the greater depths at which viable shale gas reservoirs are generally found. A problem with the shale gas approach is that porosity and, particularly, water saturation measurements, on which the Free Gas component is normally calculated, are subject to significant uncertainty.

The present applicant has a deep unconventional gas asset in the Cooper Basin (including tight sandstone, shale and coal), ranging from approximately 8,000 to 12,000+ feet, and for the reasons outlined above is experiencing difficulties accurately quantifying Total Gas content. To evaluate this resource using known techniques used by the coal seam gas industry, conventional core can be acquired (both drill pipe and wireline retrieved) and standard core desorption can be performed in an attempt to estimate the Total Gas content. Unfortunately though, the retrieval time from these depths (plus the handling time at surface) is generally in the order of 2 to 10 hours.

This strongly contrasts with what is considered "reasonable" in the shallow coal seam gas industry (which is a Lost Gas time of less than 1 hour and typically of only 15 minutes). This highlights the problem with evaluating deep zones, as is typical with many unconventional gas reservoirs. Indeed, it becomes necessary to apply a very large, highly uncertain and probably invalid, Lost Gas correction, potentially in excess of the actual amount of gas recovered.

While Option 7 may technically provide a reasonable alternative, the equipment required to undertake pressure core measurement techniques is expensive and difficult to source, and tends to introduce unnecessary (or at least undesirable) mechanical complexities.

It is an aim of the present invention to provide a more reliable and more accurate method and apparatus for the measurement of the Total Gas content of unconventional reservoir rock (be it sedimentary, igneous or metamorphic rock), and in particular for the measurement of the in-situ Total Gas content of an unconventional gas reservoir, when compared to Options 1 to 6 above, and a more convenient and cost-effective method and apparatus when compared to Option 7. In this respect, it will be appreciated that while the motivation for developing the method and apparatus of the present invention might lie in the realm of unconventional gas reservoirs, the method and apparatus will nonetheless still be usable in relation to the measurement of the in-situ Total Gas content of unconventional oil reservoirs.

Reference to any prior art in this specification is not, and should not be taken as, an acknowledgment or any form of suggestion that this prior art forms part of the common general knowledge in any country.

SUMMARY OF THE INVENTION

The present invention provides a method of measuring the in-situ Total Gas content of an unconventional reservoir rock, the method including:
a) drilling a borehole through a measurement interval in the reservoir to generate an annular volume of drilling mud that includes cuttings and gas, the annular volume having a leading edge and a trailing edge;
b) diverting the leading edge of the annular volume such that all of the annular volume is captured in a degassing storage system without being exposed to atmosphere;

c) discontinuing the diversion of the annular volume when the trailing edge of the annular volume has been captured in the degassing storage system;

d) measuring the gas volume in the degassing storage system to determine the amount of gas per annular volume; and e) calculating the in-situ Total Gas content of the reservoir with reference to the amount of gas and cuttings per annular volume.

In a preferred form, the method uses a drilling rig that includes a drilling mud circulation system and a blowout preventer through which drilling mud can be recirculated from and to the borehole during normal drilling operations. Preferably, the simultaneous closing of the blowout preventer, and opening of all valves downstream of the blowout preventer, diverts the leading edge of the annular volume such that the annular volume is captured in the degassing storage system without being exposed to atmosphere. Furthermore, preferably it is the simultaneous opening of the blowout preventer, and the closing of valves downstream of the blowout preventer terminating at the degassing storage system, when the trailing edge of the annular volume has been captured in the degassing storage system, that discontinues the diversion of the drilling mud. In this respect, the "simultaneous" opening and closing referred to is a preferred theoretical aim. It will be appreciated that reference throughout this specification to simultaneous opening and closing is a reference to opening and closing that is as near to simultaneous as practically possible.

The drilling mud may either be recirculated drilling mud or fresh drilling mud. Recirculated drilling mud will be the same drilling mud that circulates through the drilling mud circulation system during normal drilling operations and will thus have been processed by whatever separation, collection and/or treatment equipment is normally used, such as screens and sieves to remove the cuttings, filters to remove silt and sand, and purifiers, before being reintroduced to the drilling mud circulation system at an appropriate time with respect to the operation of the method of the present invention.

Fresh drilling mud may alternatively be used, and indeed may often be preferred for use, being a gas and solids-free batch of fresh drilling mud specifically prepared at a separate location to the recirculated drilling mud tanks, and introduced to the drilling mud circulation system at an appropriate time with respect to the operation of the method of the present invention. With this in mind, reference throughout this specification to "drilling mud" is to include reference to either recirculated drilling mud or fresh drilling mud unless one or other is specifically referenced as the preferred source of the drilling mud.

The present invention thus further provides a method of measuring the in-situ Total Gas content of an unconventional reservoir rock, the method using a drilling rig that includes a drilling mud circulation system that includes a blowout preventer through which drilling mud can be recirculated from and to a borehole during normal drilling operations, the method including:

a) drilling a borehole through a measurement interval in the reservoir to generate an annular volume of drilling mud that includes cuttings and gas, the annular volume having a leading edge and a trailing edge;

b) simultaneously closing the blowout preventer and opening all valves downstream of the blowout preventer to divert the leading edge of the annular volume such that all of the annular volume is captured in a degassing storage system without being exposed to atmosphere;

c) when the trailing edge of the annular volume has been captured in the degassing storage system, simultaneously opening the blowout preventer and closing valves downstream of the blowout preventer terminating at the degassing storage system to discontinue the diversion of the annular volume;

d) measuring the gas volume in the degassing storage system to determine the amount of gas per annular volume; and e) calculating the in-situ Total Gas content of the reservoir with reference to the amount of gas and cuttings per annular volume.

The present invention also provides apparatus for measuring the in-situ Total Gas content of an unconventional reservoir rock, the apparatus including:

a) a drilling rig capable of drilling a borehole through a measurement interval in the gas reservoir to generate an annular volume of drilling mud that includes cuttings and gas, the annular volume having a leading edge and a trailing edge; and b) a degassing storage system capable of capturing all of the annular volume, without the annular volume being exposed to atmosphere, when the leading edge of the annular volume is diverted thereto, the diversion being discontinued when the trailing edge of the annular volume has been captured in the degassing storage system;

whereby the gas volume in the degassing storage system can be measured to determine the amount of gas per annular volume, and the in-situ Total Gas content of the gas reservoir can be calculated with reference to the amount of gas and cuttings per annular volume.

The present invention further provides an apparatus for measuring the in-situ Total Gas content of an unconventional reservoir rock, the apparatus including:

a) a drilling rig that includes a drilling mud circulation system that includes a blowout preventer through which drilling mud can be recirculated from and to a borehole during normal drilling operations, the drilling rig being capable of drilling a borehole through a measurement interval in the gas reservoir to generate an annular volume of drilling mud that includes cuttings and gas, the annular volume having a leading edge and a trailing edge; and b) a degassing storage system capable of capturing all of the annular volume, without the annular volume being exposed to atmosphere, when the leading edge of the annular volume is diverted thereto by the simultaneous closing of the blowout preventer and opening of all valves downstream of the blowout preventer, the diversion being discontinued when the trailing edge of the annular volume has been captured in the degassing storage system by the simultaneous opening of the blowout preventer and closing of valves downstream of the blowout preventer terminating at the degassing storage system;

whereby the gas volume in the degassing storage system can be measured to determine the amount of gas per annular volume, and the in-situ Total Gas content of the gas reservoir can be calculated with reference to the amount of gas and cuttings per annular volume.

By way of explanation, the present invention thus requires a measurement interval to be drilled and preferably a full annulus of cuttings (the annular volume) generated during that measurement interval to be diverted and captured in a degassing storage system preferably located at surface as close as possible to the drilling rig. The annular volume should not be exposed to atmosphere in order to prevent any of the gas in the annular volume being lost, which requires this temporary, non-standard diversion of the drilling mud circulation system at surface (whether the drilling mud is recirculated drilling mud or fresh drilling mud).

Once captured in the degassing storage system, the cuttings are able to settle out of suspension, the gas is able to accrue in, for example, a headspace, and degassing of the entire contents of the drilling mud is able to occur over a period of time, as will be better described below.

The present invention thus permits the capture of all of the gas and cuttings in the annular volume, ideally by isolating the drilling mud circulation system from atmosphere. Indeed, rather than allowing the drilling mud to reach an open bell nipple at surface, the flow of the drilling mud will preferably be redirected down, for example, a choke line (or another suitable flow line preferably emanating from at or near the base of the blowout preventer) by closing the pipe rams or annular preventer of the blowout preventer. Such hydraulically-operated devices typically clamp around the drill pipe to seal the annular space between the drill pipe and the borehole wall, sealing the well and effectively isolating the drilling mud circulation system. Therefore, gas is unable to escape to atmosphere (via the bell nipple) until the blowout preventer is re-opened.

The end result is that all of the annular volume associated with the measurement interval of drilling, preferably with its entire gas content, is diverted to the degassing storage system rather than being recirculated in the normal manner to the drilling mud storage tanks with the gas escaping to atmosphere. In this respect, while reference is made here (and throughout the specification) to "all of the annular volume" being diverted and captured, as will be explained below it will be appreciated that it is likely that either slightly more or slightly less than the actual annular volume will probably be diverted and captured, depending upon the accuracy achievable during operation.

It will also be appreciated that a maximum of one annular volume can be captured at a time because a normal drilling operation cannot proceed while the blowout preventer is closed. However, drilling mud circulation can continue (for example, with the drill bit suspended off-bottom) which allows the annular volume to be circulated out of the borehole in the above manner for capture.

With reference to the degassing storage system and the measurement of the captured gas of the annular volume, in a preferred form of the invention the degassing storage system includes a plurality of low-positive-pressure degassing tanks used to form a combined settling and volume measurement system. In one form, at least two low-positive-pressure degassing tanks are provided, in the form of a primary degasser tank combined with one or more secondary gas measurement tanks. Prior to operation, all tanks and their associated pipework (terminating at the blowout preventer) would ideally be pre-filled with clean water (referred to herein as the "initial tank water") to a) exclude air from the system, b) maintain isolation of the annular contents from the atmosphere, and c) allow tracking of the liberated gas volume.

Preferably, three tanks would be adopted to accommodate the reservoir gas contents expected in the Cooper Basin, ideally being of identical configuration for the simplification of design, certification, fabrication and set-up in the field. Fewer or more tanks may be required in other geological provinces. To assist in understanding the context of the invention, and as will be better outlined below, the tanks would ordinarily be no larger than about 400 barrels (18 feet high× 12 feet wide) each, and ideally would be connected in series to provide fluid communication of the required type.

In the preferred Cooper Basin form, the three low-positive-pressure degassing tanks will be categorised as a primary degasser tank combined with two secondary gas measurement tanks.

Primary Degasser Tank—this tank is the first point of entry for the annular volume of the drilling mud. The primary degasser tank should be large enough to accommodate the theoretical maximum potential annular volume (including the cuttings and some of the entrained gas), and is where further gas is liberated (desorbed) from the cuttings over an extended period of time. This high-side scenario corresponds to the deepest (or in the case of horizontal drilling, the longest) unconventional gas wells likely to be drilled in geological provinces such as the Cooper Basin. Upon completion of the diversion of the annular volume, no significant gas should remain in the primary degasser tank, the tank being occupied mostly by the drilling mud (including the cuttings), with only a relatively minor volume of initial tank water stranded at the top of the tank. A sight tube on the primary degasser tank allows the drilling mud/water level to be monitored, although this may be difficult if significant mixing occurs. Even if this is not possible, the sight tube does serve a purpose in confirming that the tank is full of initial water prior to the test.

Secondary Gas Measurement Tanks—these tanks are ideally in fluid communication with the primary degasser tank and collect all gas liberated from the primary degasser tank. It is preferred to have two of these secondary gas measurement tanks connected in series in order to accommodate the largest gas volumes expected in, for example, the Cooper Basin. The secondary gas measurement tanks ideally have two main features:
1. The combined capacity to accommodate a theoretical maximum potential volume of gas. In the Cooper Basin, this scenario would correspond to a thick, fast-drilling, deep coal seam having high gas content.
2. Sight tubes enabling the Total Gas volume of the captured annular volume of drilling mud from the borehole to be measured.

However, there may be a tendency for some of the liberated gas to be lost by dissolution into the initial tank water. This applies mainly to carbon dioxide, which has high aqueous solubility at temperatures below 80° C., while methane and other hydrocarbon gases also have significant solubility in water, albeit being quite small compared to carbon dioxide. Indeed, in the case of methane, aqueous solubility decreases (at constant pressure) to a minimum at approximately 80° C. but from there increases due to a change in the solution mechanism.

Preventative measures may thus be adopted to remove or reduce the tendency for some of the liberated gas to be lost by dissolution into the initial tank water, such as:
1. The installation of heating devices in all tanks of the degassing storage system to raise the temperature of the contents to at least 80° C. This will reduce both carbon dioxide and hydrocarbon gas solubility to negligible levels, thereby forcing these gases out of solution and maximising the yield and compositional accuracy of free gas that forms in the tank headspace. This temperature should be maintained for the duration of the method of the present invention to avoid gas in the headspace being lost to solution.
2. The pre-saturation of unheated initial tank water with both carbon dioxide and hydrocarbon gases. This will also inhibit the loss of liberated gas into solution, thereby resulting in a more reliable headspace gas volume and composition. However, in this alternative, no follow-up heating would be adopted, to avoid the counting of extra gas in the headspace.

It is preferred for all tanks to be hydraulically connected in series using piping of enough size to permit both gas and water transfer by displacement, noting that the cuttings in the drilling mud do not proceed past the primary degasser tank, where they settle out. In one form of the present invention, the inlet of the primary degasser tank will be connected to the conventional choke by-pass (gut) line of a choke manifold with conventional piping so as to access the conventional blowout preventer choke line.

It will also be appreciated that the outlet of the final secondary gas measurement tank is ideally open to atmosphere via a downstream siphon-breaker to prevent gravity-drainage of the hydrostatic column in the entire tank array. In this respect, exposure of the initial tank water to atmosphere is essential because it allows displacement of the initial tank water as gas is liberated. No gas can escape from the tanks because the initial tank water forms a physical barrier.

Having mentioned the presence of a downstream siphon-breaker and the need for its special type of access to atmosphere, and as already mentioned above, all of the abovementioned tanks are ideally filled with water prior to use to also enable tracking of the liberated gas volume via the sight tubes. Indeed, it is preferred that no air should ever be present in the system, as this would eventually be measured in addition to the liberated gas and erroneously included in the Total Gas volume.

Returning to the operation of a preferred form of the present invention, when the measurement interval has been drilled, the leading edge detected at surface, and the blowout preventer subsequently closed, one annular volume of drilling mud (including cuttings and gas) is pumped down the choke line, through the choke by-pass (gut) line of a choke manifold and into the primary degasser tank. Initial water is displaced from the primary degasser tank as it fills with the drilling mud of the annular volume. By design, a certain amount of water (being the total primary degasser tank volume minus the drilling mud and cuttings volume) will remain stranded at the top of the primary degasser tank. This ensures that no drilling mud or cuttings enter the secondary gas measurement tanks, which are dedicated solely for that purpose. If excess drilling mud or cuttings do flow over, the measurement method of the present invention will not become invalid unless insufficient space remains for the Total Gas volume to be captured.

Over a period of time, which will likely be different for different geological resources and gas plays, but will probably be in the order of days to weeks, gas continues to desorb from the cuttings in the primary degasser tank and overflows into the secondary gas measurement tanks. The increase in gas volume versus time can be monitored using the sight tubes, and a final gas volume can be determined once the gas volume has stopped increasing.

Depending on the accuracy required, it may be necessary to apply a number of corrections, both positive and negative, to the gas volume physically-measured in the secondary gas measurement tanks.

The in-situ Total Gas content can then be calculated by dividing that final gas volume by the weight (preferably the dry weight) of the cuttings of the annular volume, those cuttings being the settled and dried cuttings in the primary degasser tank, with the in-situ Total Gas content typically being expressed in terms of standard cubic feet per short ton (scf/ton) "dry". Indeed, reporting Total Gas content on a "dry" basis is preferred. In this respect, unlike conventional reservoirs, where gas content "concentration" is expressed as a percentage of the rock pore space volume, gas content "concentration" of unconventional reservoirs is normally expressed as the gas volume per unit weight of rock, being the scf/ton mentioned above.

Once the measurement interval is drilled, the fluid content of the rock (now in the form of the small cuttings) is irreversibly changed and remains in a state of flux for the remainder of the process. There is also free water on the surface of the cuttings and this is something that should be avoided during the weighing step. Consistently reporting Total Gas content relative to the weight of dry cuttings normalises the Total Gas measurement and allows valid comparison to be made between separate tests.

The present invention provides advantages over several of the existing measurement techniques, in various ways. For example, a standard desorption process for core from very low permeability rocks may take several months, whereas it is anticipated that, owing to the cuttings being considerably smaller and with higher surface area, the degassing in the method of the invention will go to completion in significantly less time—and perhaps in less than one week.

Also, bulk gas composition is generally not available from standard core desorption services because gas volumes are normally measured, analysed and discarded over the course of desorption. Rarely are the sub-samples re-combined for a bulk composition measurement. However, the method of the present invention is ideal for bulk composition measurement because the entire gas volume is captured under equilibrium conditions.

Further, the present invention is ideally-suited for use with unconsolidated or naturally-fractured rocks which are prone to breaking up during coring, with resultant low recovery. The present invention ensures that all rock, whether drilled or "caved" from the wellbore wall, is transferred into the primary degasser tank and the associated gas content quantified. When degassing is complete, the weight of rock is determined by cleaning, drying and weighing the solids which have settled at the base of the primary degasser tank.

Further still, the present invention does not require any expensive tripping of the drill pipe or significant rig standby time before or after its operation. The method is simply a temporary redirection of the drilling mud circulation system while the hole continues to be drilled. Additionally, the method does not require the placement of any additional equipment down the borehole. All necessary equipment is located at surface, meaning there is thus no chance of anything being lost or stuck down-hole.

BRIEF DESCRIPTION OF THE FIGURES

The present invention will now be described in relation to a preferred embodiment of which some aspects are illustrated in the accompanying figures. In the figures.

DETAILED DESCRIPTION OF THE INVENTION

Figure 1:
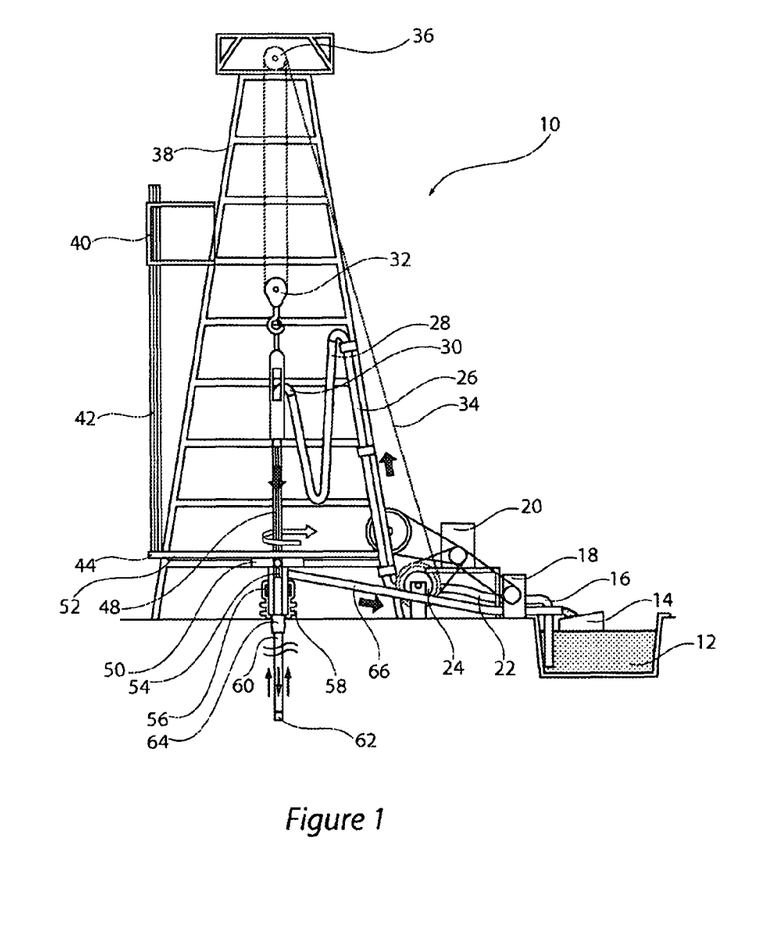
FIG. 1 is a schematic diagram of a drilling rig and a drilling mud circulation system for use with a preferred embodiment of the present invention.

Illustrated in FIG. 1 is a reasonably conventional drilling rig 10 that is able to be readily adapted for use with the present invention. The drilling rig 10 is able to be appropriately connected to a degassing storage system of the type illustrated in FIG. 2, as will be explained below. However, before describing that connection, and the operation of the method of the present invention with respect to this embodiment, a brief explanation of the components of the drilling rig 10 will be provided.

The drilling rig 10 shown in FIG. 1 includes a traditional drilling mud circulation system embodied in various elements, being drilling mud storage tanks 12, shale shakers 14, a suction line 16 for a drilling mud pump 18, and a motor 20. The pipework for these elements is embodied in a vibrating hose 22, a standpipe 26, a kelly hose 28, and culminates in a goose-neck 30. This pipework, plus a swivel or top drive for the kelly drive 48, is generally supported by a travelling block 32 hung by a drill line 34 from a crown block 36 on a derrick 38. Power for raising and lowering the travelling block 32 using the drill line 34 is supplied by the draw-works 24. Also supported from the derrick 38 is a monkey board 40, a drill pipe stand 42 and a pipe rack 44.

A rotary table 50 (driven by the motor 20) for rotating the kelly drive 48, and hence a drill string 60, is at the drill floor 52, with the arrangement of a bell nipple and blowout preventer being represented by the reference numerals 54 for the bell nipple, 56 for the annular preventer of the blowout preventer and 58 for the pipe rams and blind rams of the blowout preventer. Of course, the drill string 60 is shown below a casing head 64 and the drill bit 62 is shown schematically at the bottom of a borehole.

In terms of the normal flowpath of the recirculated drilling mud, the flow line 66 shows the path normally taken by the drilling mud (to the shale shakers 14 and the drilling mud storage tanks 12) during normal drilling operation, thus completing the drilling mud circulation system. In terms of the diverted flowpath of the drilling mud during operation of the measurement system of the present invention, this is not shown schematically in FIG. 1, but in one form would be a flowline going between the blowout preventer, via a choke manifold, to the degassing storage system (shown in FIG. 2).

However, in a preferred form, fresh drilling mud can be used in place of the recirculated drilling mud, such as a gas and solids-free batch of fresh drilling mud (which might be viscosified NaCl brine of up to 9.9 pounds per gallon concentration) specifically prepared at a separate location to the drilling mud storage tanks 12 of FIG. 1 for use in the drilling of the measurement interval.

Figure 2:
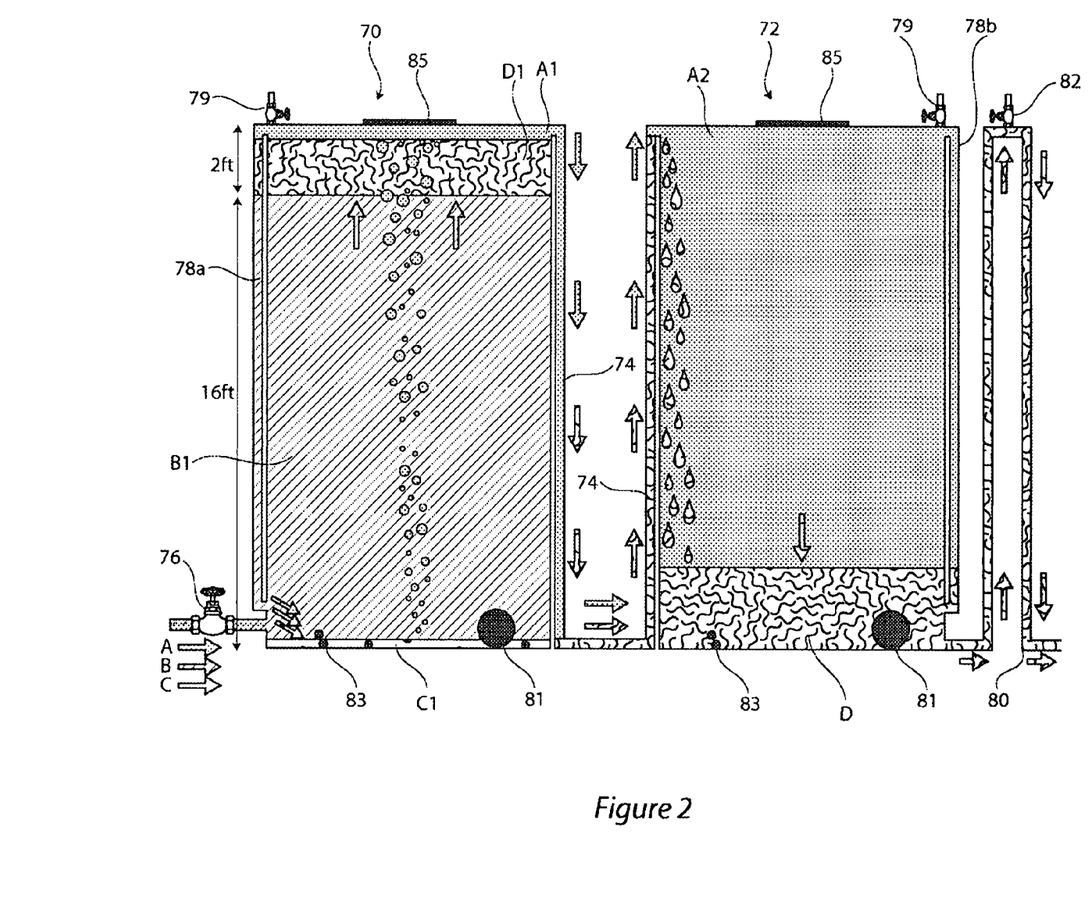
FIG. 2 is a schematic diagram of a degassing storage system for use with the preferred embodiment of FIG. 1.

Illustrated in FIG. 2 is a degassing storage system in accordance with a preferred Cooper Basin embodiment of the present invention, the operation of which will be generally described below. In terms of the degassing storage system, in this embodiment it includes three low-positive-pressure degassing tanks in the form of a primary degasser tank 70 and two secondary gas measurement tanks 72 (although only one of the secondary gas measurement tanks is illustrated in FIG. 2). All three tanks are 400 barrel customised tanks 18 feet high and 12 feet wide, connected in series by flow pipes 74 to provide fluid communication therebetween of the required type, and are preferably not fabricated from reactive materials such as aluminium, which might react with either the initial tank water or the drilling mud to produce gases such as hydrogen.

The primary degasser tank 70 is the first point of entry for the annular volume of the drilling mud, represented at the inlet valve 76 by three coded arrows A, B and C, representing liberated gas A, drilling mud B and cuttings C, the coding of the arrows (together with the coding for the initial tank water D) also being represented in the content of the tanks 70,72, the flow pipes 74 and the sight tubes 78a and 78b of the tanks 70,72. As mentioned above, the primary degasser tank 70 is large enough to accommodate the theoretical maximum potential annular volume of drilling mud (including the cuttings and some of the entrained gas), and is where further gas is liberated ("desorbed") from the cuttings over an extended period of time.

Upon completion of the diversion of the annular volume (which is the stage in the process that is generally represented in FIG. 2), no significant gas should remain in the primary degasser tank, other than the minor gas $A_1$ shown within the headspace at the top of the tank 70, the tank 70 being occupied mostly by the drilling mud $B_1$ (including the cuttings $C_1$), with only a relatively minor volume of initial water $D_1$ stranded at the top of the tank 70. The sight tube 78a on the primary degasser tank 70 allows the drilling mud/water level to be monitored.

The secondary gas measurement tank 72 is shown in fluid communication with the primary degasser tank 70 and collects all gas $A_2$ liberated from the primary degasser tank 70, where the sight tube 78b enables the Total Gas volume of the captured annular volume of drilling mud from the borehole to be measured. Having said that, and as mentioned above, it is preferred to have at least two of these secondary gas measurement tanks 72 connected in series in order to accommodate the largest gas volumes expected in, for example, the Cooper Basin, so in this embodiment it would be the secondary gas measurement tanks that together collect all gas $A_2$ liberated from the primary degasser tank 70.

All of the tanks 70,72, and all connecting pipework upstream of the final secondary gas measurement tank outlet and terminating at the blowout preventer, are pre-filled with clean water and are hydraulically connected in series using piping 74 of enough size to permit both gas and water transfer by displacement, noting that the cuttings in the drilling mud do not proceed past the primary degasser tank 70, where they settle out (noted in FIG. 2 as $C_1$). The tanks 70,72 are both shown having gas vents 79, clean-out hatches 81, liquid suction outlets 83 and explosion hatches 85.

The outlet 80 of the final secondary gas measurement tank (tank 72 in FIG. 2) is open to atmosphere via a downstream siphon-breaker 82 to prevent gravity-drainage of the hydrostatic column in the entire tank array. Of course, exposure of the initial tank water D to atmosphere is important because it allows displacement of the water D as gas A is liberated. No gas A can escape from the tanks 70,72 because the water D forms a physical barrier.

With reference to the preferred embodiment illustrated in the Figures (albeit without reproducing all of the reference numerals), the following is a step-by-step description of the operation of the method:

Step 1

Drill normally to the zone to be evaluated, and more specifically to the start of the measurement interval.

Step 2

Stop drilling at "kelly-down" if possible, kelly-down being the point at which a single joint of drilling pipe has been drilled to its maximum extent and a new joint of pipe must be connected before drilling can resume. This will minimise the number of pipe connections made while drilling the zone of interest later, noting that pipe connections have a number of undesirable effects. For example, gas may be "swabbed" into the borehole by the suction effect caused by raising the drill string bottom-hole assembly (BHA) off-bottom. This will introduce a positive error to the final Total Gas volume. If a connection is unavoidable, BHA movement in the borehole should be kept as slow as possible, thereby minimising wellbore pressure surges.

Further, the down-time associated with pipe connections increases the chance of gas migrating upwards, ahead of the leading edge of the annular volume and ahead of the first cuttings in the annulus, thereby raising the possibility of losing gas to atmosphere ahead of closing the blowout preventer. Further still, approximately 2-3 minutes of drilling mud circulation occurs while no rock is drilled, creating a "blank spot" in the annulus containing no cuttings or gas.

Once the drilling is stopped, the lithology of the rock at the start of the measurement interval should be confirmed with a bottoms-up sample.

Step 3

Case the well to the start of the measurement interval, which although being highly recommended can be regarded as optional. Casing decreases uncertainty in the Total Gas volume measurement by eliminating a number of undesirable variables, such as gas entry into the borehole from higher zones (or loss), caving of rock into the borehole from higher zones, and drilling mud losses from the borehole into higher zones (or gains).

Further, if the well has not been cased to the start of the measurement interval, it is advisable to closely monitor the background gas, drilling mud losses/gains, and drilling mud solids content, so that steps can be taken to stabilise the borehole prior to proceeding with the method. Further still, the impact on previously-drilled conventional pay zones should be considered when increasing drilling mud weight. In some situations, previously-drilled conventional pay zones can be damaged if drilling mud weight is increased too much. In addition, too high a drilling mud weight can cause drilling mud, and potentially gas and cuttings, to leak into other zones, thereby creating an error for the method of the present invention.

Step 4

Install and/or prime the degassing storage system, in this embodiment being the primary degasser tank and the two secondary measurement tanks. These tanks should ideally be positioned at the edge of the drilling lease, as close as possible to the rig, on the same side of the rig as the choke manifold and a sufficient distance from the flare pit to meet standards or regulations of the country in which the test is being conducted. This will minimise the impact on normal drilling activity and on post-drill lease activity (namely for rig-down, fracture stimulation, well completion etc).

The installation/priming process for the degassing storage system ideally includes the following:

connect the primary degasser tank inlet pipework to the choke by-pass (gut) line of the choke manifold;

connect the secondary gas measurement tanks to the primary degasser tank in series;

the outlet pipework of the final secondary gas measurement tank should be to the flare pit or drilling mud waste sump;

once the tanks have been installed, no disconnections should be necessary. Gas kicks etc (readily detectable with these tanks in place) can be resolved by directing flow through the choke and killing the well using traditional well control methods;

fill all the tanks and associated pipework (namely, everything upstream of the final secondary gas measurement tank outlet and terminating at the blowout preventer) with clean initial tank water (confirming with the sight tubes), and no air should remain;

either (a) heat the initial tank water to at least 80° C. and maintain for the duration of the operation of the method, or (b) saturate the unheated initial tank water with a gas mix similar to the expected reservoir gas composition; and optionally, install a barrier or baffle in the primary degasser tank that would inhibit mixing of the incoming drilling mud with the pre-existing water.

If the deep casing option has not been adopted, go to Step 6.

Step 5

Drill out the casing shoe and cement, if the deep casing option has been adopted, and tag the start of the measurement interval. Confirm the lithology with a bottoms-up sample. Continue circulating the drilling mud in the borehole by use of the drilling mud circulation system to obtain a constant, low background gas concentration in the circulating drilling mud. Take drilling mud samples for headspace gas analysis. This background gas can be subtracted from the Total Gas volume subsequently measured in the degassing storage system. Go to Step 7—because the presence of deep casing allows an accurate drilling mud circulation lag to be calculated from the casing internal diameter "ID".

Step 6

Determine an accurate open-hole drilling mud circulation lag time in terms of drilling mud pump strokes, in order to assist in determining when the leading edge of the annular volume is approaching the blowout preventer as the drilling mud is circulated towards surface. This determination can be attended to in the following manner:

spot a high-viscosity, coloured paint slug (a marker) on the bottom of the borehole, which at this stage is at the start of the measurement interval;

record the drilling mud pump stroke counter;

circulate (without drilling) until the marker reaches surface and detect at either the bell nipple, the possum belly or the shale shakers. The possum belly is a metal container at the head of the shale shakers that receives drilling mud from the end of the flow line. Its function is to slow the flow of drilling mud (which has gained momentum down the flow line) so that it does not spill over the shale shakers. Shale shakers are the vibrating sieves over which recirculated drilling mud passes in order to separate cuttings from the drilling mud. It does not matter which of the three locations is used to detect the marker because the time required for the marker to move between them is insignificant compared to the overall lag time. Detection at the bell nipple is preferred because this is closest to the blowout preventer where diversion to the degassing storage system occurs;

record the drilling mud pump stroke counter.

The number of strokes between spotting the marker at the bottom of the borehole and detecting it at surface gives a reliable estimate of the lag time. This is important in open hole conditions, where the theoretical annular volume may be unreliable due to wash-outs along the borehole wall. Also, and if necessary, a standard "carbide lag" can be performed as a substitute to the approach above. Having said that, the appearance of gas or cuttings at surface will always override both (a) the coloured marker and (b) a lag time estimate, when making a decision to divert the annular volume to the primary degasser tank.

Step 7

Condition the borehole. The borehole should be stable before proceeding, in terms of there being low background gas, and low drilling mud losses/gains, and the drilling mud should not contain significant solids. Any solids already within the drilling mud prior to drilling the measurement interval will settle in the primary degasser tank and create a positive error in cuttings weight. This will inaccurately reduce the calculated Total Gas content.

Step 8

If fresh drilling mud is not to be used, optionally perform a pre-measurement test as a control to quantify recirculated background gas. If there is any doubt concerning the amount of background gas in the recirculated drilling mud prior to the drilling of the measurement interval, the degassing storage system may be used to quantify this. Unfortunately though, it will take time for such gas to separate from the circulated drilling mud, which may be unacceptable for the stakeholders in the well in terms of rig time, and it will also take time to then empty the tanks and re-fill them with fresh initial tank water for the operation of the main method. It will of course be appreciated that one solution to this problem would be to have a duplicate set of degassing storage system tanks, dedicated for pre-measurement testing. Alternatively, a second solution would be to obtain a control, on a smaller scale, by degassing a drilling mud sample taken from the flowline. However, this would be less accurate due to some gas being lost to atmosphere.

Nonetheless, if it is found that the amount of background gas is high, it can simply be deducted from the subsequently determined gas volume.

It should be noted that this optional test should not be necessary if the preferred use (mentioned above) of a gas and solids-free drilling mud system is adopted to provide fresh drilling mud for the method.

Step 9

Drill the measurement interval. Immediately prior to drilling the measurement interval, spot a high-viscosity, coloured paint slug on bottom to mark the start of the measurement interval, to inhibit the rise of gas ahead of the cuttings, and to serve as a visible marker preceding the leading edge of the drilling mud at surface (which tends to be more reliable than the lag time estimate). While drilling from the start of the measurement interval to the end of the interval, optimise the drilling parameters to obtain the highest possible rate of penetration (ROP) for the lowest pump rate. This will generate the highest concentration of cuttings and gas in the annular volume generated during the drilling.

Stop drilling and pick up off bottom as soon as the marker reaches surface. The lag time will only be used as a guide for when cuttings and gas are likely to appear at surface, particularly if there is no deep casing. As mentioned above, the actual appearance of gas or cuttings should override all other indicators.

At this point, the annulus now contains all drilled cuttings and associated gas from the measurement interval, dispersed along the borehole from the total depth (TD) to surface, being the annular volume which is marked at its leading edge.

The drilling mud circulation should be maintained to avoid settling of the cuttings. Should any cuttings move below the drill bit (which is suspended off-bottom), they become difficult to lift.

Once the leading edge of the annular volume approaches the blowout preventer, the following diversion step should be performed without delay, otherwise the drilling mud will be pumped to surface through the blowout preventer and through the bell nipple. In that event, the entrained cuttings would be lost to the drilling mud waste sump and the gas would be lost to atmosphere.

Step 10

Divert the annular volume to the degassing storage system. To divert the complete annular volume of the drilling mud to the primary degasser tank, the following two operations should occur simultaneously (or near to simultaneously):

1. Open all valves upstream and downstream of the primary degasser tank to avoid a pressure spike in the annulus when the blowout preventer is closed. There should be an uninterrupted flow path to atmosphere from the choke line outlet of the blowout preventer, through the degassing storage system, to the flare pit or the drilling mud waste sump. It will be appreciated that when the annular contents subsequently enter the degassing storage system, at no stage is there direct contact with the atmosphere. This is because the initial tank water forms a physical barrier. No gas can escape.
 2. Close the blowout preventer to seal the annulus. This diverts the drilling mud, cuttings and entrained gas through the choke line and choke manifold and into the primary degasser tank.

Immediately these two actions are taken, or simultaneously therewith, circulate a high-viscosity slug to the bottom of the borehole (marking the trailing edge of the annular volume) to help lift the final cuttings. A colour marker is not required because visual monitoring is difficult to achieve along the closed flowpath leading to the primary degasser tank. Indeed, instead of using a visible marker to determine the arrival of the trailing edge of the annular volume at the surface, the time lag determination (and thus the number of previously-determined drilling mud pump lag strokes) can be used. With this in mind, continue pumping of the drilling mud circulation system for one such lag time.

The trailing edge of the annular volume should now be at the blowout preventer and the full annular volume diverted to the primary degasser tank (time lag and drilling mud/cuttings/gas volume between the blowout preventer and the tank is insignificant). The bottom-hole pressure can be maintained constant while circulating cuttings and gas to surface by maintaining circulation pressure (standpipe pressure) constant.

During this step, the standpipe pressure and the outlet of the last of the secondary gas measurement tanks must be continuously monitored at all times for kick detection and surface line blockage. In the remote event that the choke line or the choke manifold becomes blocked (indicated by a rising standpipe pressure), divert the drilling mud to the flow line and attempt to clear the blockage. Confirm pressure and, if necessary, perform the standard well control procedure. If a gas kick evolves, indicated by either a) a falling standpipe pressure or b) an increased displaced-water flow at the outlet of the last secondary gas measurement tank, abort the test and initiate standard well control procedure (e.g. the driller's method).

With the trailing edge of the annular volume now at the blowout preventer and the full annular volume diverted to the primary degasser tank, shut down the drilling mud pumps and close the choke line and inlet to the primary degasser tank. All valves downstream of the primary degasser tank inlet should be left open, to allow for gas expansion and initial tank water expulsion during the ongoing degassing process. If this is not done, pressure in all tanks will increase, inhibiting gas liberation from the cuttings and possibly exceeding the burst rating of the pressure relief valves.

Establish that the shut-in pressure of the borehole is zero, perform a flow check through the choke line prior to opening the blowout preventer, and open the blowout preventer, redirecting the drilling mud stream back to its conventional path through the blowout preventer and the bell nipple, down the flow line to the drilling mud storage tanks.

All of the drilling mud (including the cuttings and associated gas) of the annular volume generated during the drilling of the measurement interval has now been captured in the primary degasser tank, so that normal drilling can be resumed.

Step 11

Leave the degassing storage system (including the primary degasser tank and the secondary gas measurement tanks) in position for the duration of gas liberation. With the inlet of the primary degasser tank now closed, the pipework to the choke manifold may be disconnected. However, as the tanks will be too heavy to transport once filled, they would be left in place. Indeed, as much as 2,000+ standard cubic feet of gas per short ton of cuttings (in the case of coal) may accumulate in the secondary gas measurement tanks and as much as one short ton of cuttings may settle in the primary degasser tank.

Record the increasing gas volume in the secondary gas measurement tanks at regular intervals using the sight tubes on each tank. The time required for degassing to go to completion will vary according to properties of the rock involved. It is estimated that this may take days to weeks.

Step 12

Empty all tanks but retain the cuttings from the primary degasser tank. Collecting, drying and weighing the cuttings accumulated at the bottom of the primary degasser tank enables the Total Gas volume per weight of associated rock to be calculated and expressed as scf/ton "dry".

Vent the gas in all tanks to atmosphere in a controlled manner, drain all drilling mud from the primary degasser tank via the liquid suction outlets, drain all initial tank water from the secondary gas measurement tanks, and remove all cuttings from the primary degasser tank, placing the cuttings in a suitable container (e.g. a "mini-skip") to be washed with water to remove all foreign material (particularly any high-density barite associated with the drilling mud). In this respect, if the preferred form of a fresh drilling mud, being a gas and solids-free drilling mud system, was adopted as the drilling mud, only minimal washing of the cuttings will be required.

Once empty, the tanks may be transported to the next well location for re-use.

Step 13

Sample the cuttings, in advance of drying, for residual gas analysis. Collect a small sub-sample of cuttings and send this to a core desorption laboratory for residual gas analysis. This will quantify the small amount of residual gas not yet liberated (standard procedure for conventional core desorption). The sample should be kept on ice during transportation.

Step 14

Sample the cuttings, in advance of drying, for other analyses. A number of important tests can be performed on the degassed cuttings such as adsorption, proximate analysis, Total Organic Carbon (TOC), RockEval, porosity, permeability, density, Scanning Electron Microscopy (SEM), X-Ray Diffraction (XRD), and maceral analysis etc, so additional small sub-samples should be taken as required.

Step 15

Record the total dry weight of cuttings. After sub-sampling, dry the cuttings thoroughly, and then place the cuttings in a suitable container for weighing. Add back the dry weight of sub-samples previously taken.

Step 16—the Final Step

Calculate the in-situ Total Gas content for the measurement interval. The in-situ Total Gas content can be calculated by dividing the gas volume measured by the method of the present invention (for the annular volume) by the dry weight of the cuttings in the annular volume. The in-situ Total Gas content can then be expressed in terms of scf/ton "dry". Corrections can be applied as required (e.g. to add residual cuttings gas to the gas volume measured in the tanks), and standardisations can be applied as required (e.g. convert to "dry-ash free" in the case of coal).

It should also be noted that a "reality check" can be performed on the cuttings weight by using standard electric logging caliper measurements to calculate the hole volume created over the measurement interval. By applying the density of the cuttings collected from the primary degasser tank, the weight of drilled rock can be determined Further, depending on the accuracy required, it will be appreciated that it may be necessary to apply a number of corrections, both positive and negative, to the gas volume physically-measured in the secondary gas measurement tanks.

In terms of the preferred specifications for the tanks ideally adopted for use in the degassing storage system, the primary degasser tank should be large enough to contain high-side scenarios for the expected annular volumes. This is a function of a) borehole/casing diameter and b) depth to the measurement interval. For example, it is envisaged for the Cooper. Basin that the high-side annular volume should be set at 350 barrels, based upon the theoretical high-side annular volume being 324 barrels. This theoretical value equates to the total annular volume associated with the deepest likely, standard hole size, Cooper Basin unconventional vertical gas well having 7⅝" surface casing to approximately 3,000 feet and 6¾" open-hole to 10,000 feet. From 3,000 to 10,000 feet, the annular volume is defined by 3½" drill-pipe and 4¾" drill collars in open-hole.

Such boreholes are invariably overgauge by approximately 10%, so the practical high-side annular volume therefore becomes 350 barrels. Nevertheless, severely overgauge hole need not be a limiting factor for the method and it will be appreciated that there is no requirement for a full (and entirely accurate) annular volume to be sampled. Indeed, when the primary degasser tank is almost full of annular contents, it will be appreciated that the diversion could be terminated by closing the blowout preventer.

Furthermore, the theoretical maximum volume of cuttings collected in the annulus during the drilling of the measurement interval, and subsequently diverted to the primary degasser tank within the annular volume is a function of a) borehole diameter, b) ROP and c) the drilling mud circulation lag time from the bottom of the hole to surface.

Based on a lag time of approximately 40 minutes at 10,000 feet, and a fast ROP of 0.5 minute per foot (deep coal scenario), 80 feet of 6¾" hole will be drilled.

This will generate approximately 0.6 cubic meters of cuttings if the hole is relatively in-gauge. If the hole is caved, significantly more cuttings may result but this does not create a problem because everything is captured and measured at surface.

It is unlikely that extra (caved) cuttings would cause the drilling mud in the primary degasser tank to overflow into the adjacent secondary gas measurement tank because the volumetric proportion of the cuttings in the primary degasser tank is initially quite minor (4 barrels in 400 or 1%) and there is at least a 46 barrel capacity of undisplaced tank water available to accommodate considerably more. Cavings, provided they are only from the measurement interval, are actually a positive outcome. The resulting higher concentration of cuttings and gas in the annulus will give a more reliable Total Gas measurement in the degassing storage system.

If the high-side annular volume is displaced to the pre-water-filled, 400 barrel primary degasser tank (being a tank 18 feet high×12 feet wide), the respective height components of the various separated fluids and solids would be as follows:

Headspace gas=negligible (gas is continually displaced to the headspace of the secondary gas measurement tanks)

Stranded water=1.8 feet (46 barrels)

Drilling Mud=16 feet (350 barrels)

Cuttings=0.2 feet (4 barrels)

The high-side cuttings volume (0.6 cubic meter) represents approximately 0.9 short tons of rock, based on a typical coal bulk density of around 1.3 grams per cubic centimeter (or metric tonnes per cubic meter).

The secondary gas measurement tanks should have the combined capacity to accommodate the theoretical maximum potential volume of gas liberated in the primary degasser tank.

To arrive at a high-side gas volume estimate, evidence for high-side gas content must be first be found. This is provided by an anomalous desorption test performed on a Cooper Basin deep coal, where the in situ Total Gas content was estimated to be in the order of 2,000 scf/ton ("dry ash free")—albeit with high uncertainty. Given that the primary degasser tank may contain 0.9 short tons of coal cuttings (or more), this represents a high-side gas volume in the order of 1,900 scf (approximately 340 barrels).

The practical limit on the size of any of the tanks is 400 barrels. To allow for potentially larger gas volumes caused by caving (particularly prevalent in coals), it is necessary to connect two tanks of this size in series. This creates a large amount of excess capacity, ensuring that, even in a caved-hole situation, a higher-than-expected gas volume will never displace all the initial water from the tanks.

A person skilled in the art will understand that there may be variations and modifications other than those specifically described. It is to be understood that the invention includes all such variations and modifications. The invention also includes all of the steps, features, compositions and compounds referred to, or indicated in this specification, individually or collectively, and any and all combinations of any two or more of the steps or features.

The invention claimed is:

1. A method of measuring the in-situ Total Gas content of an unconventional reservoir rock, the method including:
   a) drilling a borehole through a measurement interval in the reservoir to generate an annular volume of drilling mud that includes cuttings and gas, the annular volume having a leading edge and a trailing edge;
   b) diverting the leading edge of the annular volume such that all of the annular volume is captured in a degassing storage system without being exposed to atmosphere;
   c) discontinuing the diversion of the annular volume when the trailing edge of the annular volume has been captured in the degassing storage system;
   d) measuring the gas volume in the degassing storage system to determine the amount of gas per annular volume; and
   e) calculating the in-situ Total Gas content of the reservoir with reference to the amount of gas and cuttings per annular volume.

2. A method according to claim 1, wherein the method uses a drilling rig that includes a drilling mud circulation system and a blowout preventer through which drilling mud is recirculated from and to the borehole during normal drilling operations.

3. A method according to claim 2, wherein the simultaneous closing of the blowout preventer and opening of all valves downstream of the blowout preventer diverts the leading edge of the annular volume such that all of the annular volume is captured in the degassing storage system without being exposed to atmosphere.

4. A method according to claim 2, wherein, when the trailing edge of the annular volume has been captured in the degassing storage system, the simultaneously opening of the blowout preventer and the closing of valves downstream of the blowout preventer terminating at the degassing storage system, discontinues the diversion of the annular volume.

5. A method according to claim 1, wherein, once captured in the degassing storage system, the cuttings settle out of suspension, and degassing of the drilling mud occurs over a period of time.

6. A method according to claim 5, wherein the degassing storage system includes a plurality of low-positive-pressure degassing tanks used to form a combined settling and volume measurement system, the degassing tanks initially being filled with clean water before diversion of the annular volume thereto and each having a potential headspace for gas accumulation.

7. A method according to claim 6, including at least two low-positive-pressure degassing tanks in the form of a primary degasser tank combined with one or more secondary gas measurement tanks.

8. A method according to claim 7, wherein the secondary gas measurement tanks are connected in series and are in fluid communication with the primary degasser tank to collect substantially all of the gas liberated from the primary degasser tank.

9. A method according to claim 7, wherein the secondary gas measurement tanks include sight tubes to enable tracking of the liberated gas volume.

10. A method according to claim 7, wherein upon completion of the diversion of the annular volume and subsequent degassing, no significant gas remains in the primary degasser tank, the space being occupied mostly by the drilling mud and the cuttings, with only a relatively minor volume of initial water remaining at the top of the tank.

11. A method according to claim 7, wherein an outlet of the final secondary gas measurement tank is open to atmosphere via a downstream siphon-breaker to prevent gravity-drainage of the degassing storage system, providing exposure of the initial tank water to atmosphere to allow displacement of the water as gas is liberated.

12. A method according to claim 7, wherein the initial tank water is pre-saturated with dissolved gas, of representative composition, to prevent loss of liberated gas into solution.

13. A method according to claim 7, wherein the initial tank water is heated to at least 80° C. to reduce both carbon dioxide and hydrocarbon gas solubility to negligible levels, thereby forcing these gases out of solution.

14. A method according to claim 1, wherein fresh drilling mud in the form of a gas and solids-free drilling mud is used as the drilling mud.

15. A method of measuring the in-situ Total Gas content of an unconventional reservoir rock, the method using a drilling rig that includes a drilling mud circulation system that includes a blowout preventer through which drilling mud is recirculated from and to a borehole during normal drilling operations, the method including:
   a) drilling a borehole through a measurement interval in the reservoir to generate an annular volume of drilling mud that includes cuttings and gas, the annular volume having a leading edge and a trailing edge;
   b) simultaneously closing the blowout preventer and opening all valves downstream of the blowout preventer to divert the leading edge of the annular volume such that all of the annular volume is captured in a degassing storage system without being exposed to atmosphere;
   c) when the trailing edge of the annular volume has been captured in the degassing storage system, simultaneously opening the blowout preventer and valves downstream of the blowout preventer terminating at the degassing storage system to discontinue the diversion of the annular volume;

d) measuring the gas volume in the degassing storage system to determine the amount of gas per annular volume; and e) calculating the in-situ Total Gas content of the reservoir with reference to the amount of gas and cuttings per annular volume.

16. Apparatus for measuring the in-situ Total Gas content of an unconventional reservoir rock, the apparatus including:

a) a drilling rig capable of drilling a borehole through a measurement interval in the gas reservoir to generate an annular volume of drilling mud that includes cuttings and gas, the annular volume having a leading edge and a trailing edge; and b) a degassing storage system capable of capturing all of the annular volume, without the annular volume being exposed to atmosphere, when the leading edge of the annular volume of the drilling mud is diverted thereto, the diversion being discontinued when the trailing edge of the annular volume has been captured in the degassing storage system;

whereby the gas volume in the degassing storage system can be measured to determine the amount of gas per annular volume, and the in-situ Total Gas content of the gas reservoir can be calculated with reference to the amount of gas and cuttings per annular volume.

17. Apparatus according to claim 16, wherein the apparatus includes a drilling mud circulation system that includes a blowout preventer through which drilling mud is recirculated from and to a borehole during normal drilling operations.

18. Apparatus according to claim 17, wherein the leading edge of the annular volume is diverted to the degassing storage system by simultaneously closing the blowout preventer and opening all valves downstream of the blowout preventer.

19. Apparatus according to claim 17, wherein the diversion of the annular volume to the degassing storage system is discontinued by simultaneously opening the blowout preventer and closing valves downstream of the blowout preventer terminating at the degassing storage system.

20. Apparatus according to claim 16, wherein the degassing storage system includes a plurality of low-positive-pressure degassing tanks used to form a combined settling and volume measurement system.

21. Apparatus according to claim 20, including at least two low-positive-pressure degassing tanks in the form of a primary degasser tank combined with one or more secondary gas measurement tanks.

22. Apparatus according to claim 21, wherein the secondary gas measurement tanks are connected in series and are in fluid communication with the primary degasser tank to collect all gas liberated from the primary degasser tank.

23. Apparatus according to claim 21, wherein the secondary gas measurement tanks include sight tubes to enable tracking of the liberated gas volume.

24. Apparatus according to claim 21, wherein an outlet of the final secondary gas measurement tank is open to atmosphere via a downstream siphon-breaker to prevent gravity-drainage of the degassing storage system.

25. An apparatus for measuring the in-situ Total Gas content of an unconventional reservoir rock, the apparatus including:

a) a drilling rig that includes a drilling mud circulation system that includes a blowout preventer through which drilling mud is recirculated from and to a borehole during normal drilling operations, the drilling rig being capable of drilling a borehole through a measurement interval in the gas reservoir to generate an annular volume of drilling mud that includes cuttings and gas, the annular volume having a leading edge and a trailing edge; and b) a degassing storage system capable of capturing all of the annular volume, without the annular volume being exposed to atmosphere, when the leading edge of the annular volume of the drilling mud is diverted thereto by the simultaneous closing of the blowout preventer and opening of all valves downstream of the blowout preventer, the diversion being discontinued when the trailing edge off the annular volume has been captured in the degassing storage system by the simultaneous opening of the blowout preventer and closing of valves downstream of the blowout preventer terminating at the degassing storage system;

whereby the gas volume in the degassing storage system can be measured to determine the amount of gas per annular volume, and the in-situ Total Gas content of the gas reservoir can be calculated with reference to the amount of gas and cuttings per annular volume.

\* \* \* \* \*

UNITED STATES PATENT AND TRADEMARK OFFICE
CERTIFICATE OF CORRECTION

| | | |
|---|---|---|
| PATENT NO. | : 8,714,004 B2 | Page 1 of 1 |
| APPLICATION NO. | : 13/522201 | |
| DATED | : May 6, 2014 | |
| INVENTOR(S) | : Erik Christopher Dunlop et al. | |

It is certified that error appears in the above-identified patent and that said Letters Patent is hereby corrected as shown below:

In the Claims

At column 20, line 67, immediately after, "opening the blowout preventer and", please insert --closing--.

Signed and Sealed this
Sixteenth Day of September, 2014

Michelle K. Lee
*Deputy Director of the United States Patent and Trademark Office*